United States Patent [19]

Pascal et al.

[11] 4,243,814

[45] Jan. 6, 1981

[54] PROCESS FOR THE CHEMICAL CATALYTIC HYDROLYSIS OF AN α-AMINONITRILE OR OF ONE OF THE SALTS THEREOF

[76] Inventors: Robert Pascal, rue des Bruces Batiment F la Satem, Montpellier, France, 34000; Monique Lasperas nee Marnier, Pioch 2 Baillos - Route de St-Clement, Montferrier sur Lez, France, 34; Alain Rousset, 314 rue de l'Aiguelongue, Montpellier, France, 34000; Auguste Commeyras, Impasse des Ecoles, Clapiers, France, 34170; Jacques Taillades; Louis Mion, 477 rue d'Alco, Montpellier, France, 34000

[21] Appl. No.: 856,320

[22] Filed: Dec. 1, 1977

[30] Foreign Application Priority Data

Dec. 3, 1976 [FR] France ................................ 76 36520

[51] Int. Cl.$^3$ ................. C07D 233/26; C07D 209/20; C07D 207/09; C07C 99/10
[52] U.S. Cl. .................................. 548/344; 548/343; 562/443; 562/445; 562/559; 562/562; 562/563; 562/570; 562/573; 562/575; 260/326.2; 260/326.14 T; 564/162; 564/164; 564/165; 564/192; 564/198
[58] Field of Search ............................. 548/343, 344; 260/534 C, 326.2, 326.14 T; 562/575, 570, 573, 559, 562, 563, 443, 445

[56] References Cited

U.S. PATENT DOCUMENTS

| | | | |
|---|---|---|---|
| 2,004,523 | 6/1935 | Fick ....................................... | 562/575 |
| 3,267,130 | 8/1966 | Kato et al. ........................... | 562/575 |
| 3,536,726 | 10/1970 | Fink et al. .................... | 260/326.14 T |
| 3,867,436 | 2/1975 | Nakamura et al. .................. | 562/443 |
| 4,072,698 | 2/1978 | Hylton ................................ | 562/443 |

FOREIGN PATENT DOCUMENTS 908735 10/1962 United Kingdom ..................... 562/562

OTHER PUBLICATIONS

Williams, An Introduction to Organic Chemistry, 3rd Ed., Von Nostrand, N.Y., p. 102.
Conant, The Chemistry of Organic Compounds, MacMillan, N.Y., 1939, pp. 120-121.

*Primary Examiner*—Henry R. Jiles
*Assistant Examiner*—Natalia Harkaway
*Attorney, Agent, or Firm*—Dressler, Goldsmith, Shore, Sutker & Milnamow, Ltd.

[57] ABSTRACT

A process for the chemical catalytic hydrolysis of an α-aminonitrile or of one of the salts thereof, characterized in that an aqueous solution containing at least one carbonyl derivative is reacted with the said α-amine nitrile or with one of the salts thereof in the presence of hydroxide ions.

11 Claims, No Drawings

PROCESS FOR THE CHEMICAL CATALYTIC HYDROLYSIS OF AN α-AMINONITRILE OR OF ONE OF THE SALTS THEREOF

The present invention relates to a process for chemical catalytic hydrolysis of α-amino nitriles or of the salts thereof. In accordance with the process of the invention, this catalytic hydrolysis of an α-amino nitrile or of one of the salts thereof may lead, depending on the particular reaction conditions, either to the formation of an α-amino amide, or to the formation of an α-amino acid salt, the latter being readily transformed into the corresponding free α-amino acid by neutralisation.

The present invention therefore also relates particularly to the preparation of α-amino acids in the form of their racemic mixture from α-amino nitriles or salts thereof or even from the precursors thereof, if any. It should be remembered that the α-amino acids are of incontestable industrial value. Some of them may, in fact, be used in human or veterinary medicine as well as in food, for example, for making up the intake of food. Some of the derivatives may also be used, for example, in the composition of soaps or cosmetics.

Up to the present, these α-amino acids have usually been prepared by the so-called "Bucherer-Berg" method. In this method, the ammonium carbonate acid acts on the intermediary α-amino nitrile to form a hydantoin which is subsequently hydrolysed in a basic medium for obtaining an α-amino acid salt. This process has a marked degree of effectiveness since it allows up to 90% of the starting aldehyde to be transformed into α-amino acid. However, it is still difficult in terms of technology since it involves:

the use of non-recoverable excess of ammonium carbonate acid;

Two heating phases; the first for two hours at temperatures of the order of from 80° to 100° C. for forming the hydrantoin and the second for about 6 hours at temperatures of the order of from 120° to 125° C. for effecting hydrolysis; and the formation of 1.5 mole of Na$_2$SO$_4$, of very low economic value, per mole of α-amino acid prepared by this process.

In spite of the disadvantages of this process, this method has been widely preferred to that of "STRECKER" which consists in hydrolysing the α-amino nitrile immediately into α-amino amide and then into α-amino acid, owing to the yield of less than 80% which has always been obtained when transforming the starting aldehydes into α-amino acid.

The present invention therefore relates to a process of chemical catalytic hydrolysis of an α-amino nitrile or of one of the salts thereof, according to which an aqueous solution containing at least one carbonyl derivative is reacted with the said α-amino nitrile or with one of the salts thereof in the presence of hydroxide OH$^-$ ions.

According to another feature of the process of the invention, the minimum water content of the reaction medium is 1 mole of water per mole of α-amino nitrile, thus allowing the carbonyl derivative to be regenerated.

According to another feature of the process for chemical catalytic hydrolysis of the invention, the hydroxide ions are introduced in a small quantity in to the aqueous reaction medium, preferably in a proportion of from 0.1 to 0.3 mole of hydroxide per mole of starting α-amino nitrile, and the corresponding α-amino amide thus obtained is then extracted.

According to another feature of the present invention, the hydroxide ions are introduced into the aqueous reaction medium so as to attain substantially equimolarity of the hydroxide in proportion to the starting α-amino nitrile in order to prepare the corresponding free α-amino acid.

The process for chemical catalytic hydrolysis according to the invention applies particularly to α-amino nitriles corresponding to the general formula (I)

in which the radical R represents a hydrogen atom or a linear or branched hydrocarbon chain containing from 1 to 12 carbon atoms and optionally 1 or several heteroatoms such as sulphur, the said radical R optionally being substituted one or more times, preferably at the end of the chain, by groups such as hydroxyl, amino, carboxyl, phenyl, hydroxyphenyl, carboxamido, indolyl, imidozolyl and guanidyl, or R forms with the nitrogen atom in the α position a saturated heterocyclic group containing at least 1 hetero atom such as nitrogen, the said heterocyclic group itself being optionally substituted, for example by a hydroxyl group, or to one of the salts thereof.

Other features and advantages of the present invention will be seen when reading the detailed description below.

It has been observed that by adding an α-amino nitrile or one of the salts thereof, such as, for example, the hydrochloride in an aqueous solution containing a carbonyl derivative and hydroxide ions, the α-amino amide corresponding to the starting α-amino nitrile was very rapidly obtained quantitatively, even at ambient temperature. In order to carry out the process according to the invention, the OH$^-$ hydroxide ions are brought in the reaction medium, for example, in the form of a hydroxide of an alkaline or alkaline-earth metal or even in the form of ammonium hydroxide.

Suitable carbonyl derivatives for catalysing hydrolysis of the α-amino nitriles mainly include the ketones of low molecular weight, owing to their good solubility in the medium and their volatility. Examples of suitable carbonyl derivatives include acetone, methylethyl ketone, diethyl ketone, methyl isopropyl ketone ethyl isopropyl ketone, and mixtures of these ketones. It should be noted that the lack of solubility may be compensated by using a dilute alcoholic solution or even by adding a hydrophilic function to the molecule of the carbonyl derivative.

The various experiments conducted have also demonstrated that the aldehydes are active from the catalytic point of view but tend to polymerise in a basic medium and are thus less valuable than the ketones. It will also be observed that the carbonyl derivative acts as a catalyst at all concentrations. Experience has shown, for example, that acetone converts α-amino methyl mercapto propionitrile quantitatively as soon as its concentration reaches 0.1 mole per liter. According to the process of the invention, the carbonyl derivative is preferably introduced into the reaction medium in a proportion of from 0.1 to 2 moles, and preferably from 0.1 to 1 mole, of carbonyl derivative, per mole of starting α-amino nitrile. It should be specified that in the case of a sparingly soluble α-amino nitrile, a higher concentration of ketone may promote solubility at the same time as the hydrolysis reaction. In such a case, the reaction may also be advantageously conducted in a dilute alcoholic solution.

Once the α-amino acid has formed in the reaction medium thus completing the hydroxide concentration in the solution obtained, until the hydroxide concentration is substantially equal to or slightly higher than that of the starting nitrile, the salt, for example the alkaline salt, of the α-amino acid corresponding to the starting nitrile is then obtained. In order to promote this second stage of chemical catalytic hydrolysis according to the invention, the reaction medium is advantageously heated to a temperature of the order of 80° C., for example for a period of about 1 hour.

It is then sufficient to neutralise the medium for example using sulphuric acid, and the free α-amino acid may then be extracted by crystallisation or by any other known method. The yield of free α-amino acid is substantially quantitative in proportion to the starting nitrile. It should be noted that the process according to the invention leads to the α-amino acids in the form of their racemic mixtures which may, of course, be separated into their optical isomers by well known conventional methods. In this particular case, a half-mole of $Na_2SO_4$ is formed per mole of free α-aminated acid.

During the heating process required for promoting and accelerating the reaction for hydrolysing the α-amino amide into α-amino acid, the carbonyl derivative used for catalysing the reaction may distil and may thus be recovered and reused for a later operation. It will also be observed that a mole of ammonia has been formed during this same reaction. It may also be recycled and reused for the production of a new molecule of α-amino nitrile.

During the stage of hydrolysing the α-amino nitrile into the corresponding α-amino amide, the catalysing carbonyl derivative must be associated with the $OH^-$ hydroxide ions which may be introduced into the medium with the carbonyl derivative, for example, advantageously in the form of an alkaline metal hydroxide such as in the form of soda. The concentration of hydroxide ions required for catalysis is also variable and is comprised between traces and a concentration very much higher than that of the α-amino nitrile. More specifically, it is comprised between 0.1 and 3 mole per mole of starting α-amino nitrile. It is observed that a concentration of alkaline hydroxide which is too much higher than that of α-amino nitrile only leads to an increase in the velocity of the stage for hydrolysing α-amino amide into α-amino acid, but leads to the subsequent production of a larger quantity of sodium sulphate.

According to a variation of the process of the present invention, the α-amino nitrile is prepared in situ in the reaction mixture intended to undergo chemical catalytic hydrolysis. It is therefore possible to synthesise α-amino acid from α-amino nitriles prepared in situ in aqueous or dilute alcoholic solutions initially containing:

(a) a cyanohydrin and ammonia; or
(b) an aldehyde, hydrocyanic acid and ammonia; or
(c) an aldehyde, a cyanide, for example an alkaline cyanide, ammonia and an ammonium salt.

It has thus been shown that it was necessary to form α-amino nitrile in the first stage, to transform it into α-amino amide in the second stage by using the catalytic conditions described above, and finally to hydrolyse the α-amino amide obtained into the α-amino acid in the third stage, also under the conditions described above.

Whatever the composition of the starting solutions defined under point (a), (b) and (c), the conditions for forming α-amino nitriles are known from the mechanistic and thermodynamic points of view. As described in the article by A. COMMEYRAS et Coll. in the journal "Information Chimie" No. 158 (1967) pages 199 to 207, examination of the results given in this publication allow a conclusion to be drawn that once equilibrium is obtained the rate of conversion of the α-amino nitrile in relation to the aldehyde or the starting cyanohydrin increases proportionately to the concentration of ammonium in basic form to the concentration of aldehyde or of starting cyanohydrin for a pH above 11.

For example, in the case of acetaldehyde and at 35° C. in the case of an initial equimolar proportion of aldehyde and HCN or $CN^-$, the rate of conversion into α-amino propionitrile varies as a function of the starting concentration of aldehyde expressed in mole per liter and of the starting concentration of $NH_3$ also expressed in mole per liter as shown in table 1 below.

TABLE 1

| | starting concentration of $NH_3$ in mole/liter. | 1 | 5 | 10 | 20 | 40 |
|---|---|---|---|---|---|---|
| For a starting concentration of $CH_3CHO$ and HCN equal to 0.5 mole/l. | conversion rate into α-aminopropionitrile | 73% | 94% | 97% | 98.5% | 99.2% |
| For a starting concentration of $CH_3CHO$ and HCN equal to 1 mole/l. | starting concentration of $NH_3$ in mole/liter conversion rate into α-aminopropionitrile | 1 56% | 5 88% | 10 94% | 20 97% | 40 98.4% |
| For a starting concentration of $CH_3CHO$ and HCN equal to 2 moles/l. | starting concentration of $NH_3$ in mole/liter conversion rate into α-aminopropionitrile | 1 37% | 5 78% | 10 88% | 20 94% | 40 97% |

Under such conditions, it appears clearly that the optimum to be defined for forming an α-amino nitrile can only be an economic optimum since it is, in fact, possible to theoretically obtain an quantitative conversion of the aldehyde into α-amino nitrile.

During the various experiments carried out, it has particularly been found with regard to this stage of α-amino nitrile formation that the use of an excess of between 1 and 10% of HCN or $CN^-$ in proportion to the cyanide contained in the equimolar aldehyde-cyanide system stabilised the α-amino nitrile solution obtained.

It has then been shown that by adding to the α-amino nitrile solution prepared and optimised as described above a carbonyl derivative and mainly a ketone selected from those listed above and combined with an alkaline hydroxide in the proportions also given above, the α-amino nitrile of the medium was catalytically transformed into α-amino amide. This conversion of the α-amino nitrile into α-amino amide is very rapid and almost quantitative in relation to the concentration of α-amino nitrile present in the medium at equilibrium.

The experiments have then shown that by increasing the concentration of alkaline hydroxide in the solution thus prepared to the equivalent of or slightly above (between 5 and 10%) the concentration of starting α-amino nitrile, and preferably by heating the reaction medium thus obtained, the α-amino amide contained in the solution was quantitatively converted into alkaline salt of the corresponding α-amino acid. As described above, after neutralisation, for example by means of sulphuric acid, the free α-amino acid is obtained and recovered by known methods. The molar quantity of sodium sulphate formed in the medium is thus slightly greater than half of the molar quantity of α-amino acid. A quantity of ammonia which is eqivalent to the quantity of α-amino amide contained in the medium is also formed during this stage. This ammonia is recovered and may be reused. The ketone which catalyses this hydrolysis reaction also distils during this stage and may thus be recovered then recycled.

In the scope of the present invention, it should be noted that during the first phase of catalytic conversion of the α-amino nitrile into the corresponding α-amino amide, the formation was observed of a reactive intermediary known hereinafter as "Y" intermediary, the structure of which could not however be determined with complete certainty. Nevertheless, the very existence of this "Y" intermediary affirms quite definitely that the carbonyl compound introduced into the reaction medium does in fact act as a catalyst.

Thus in the case of chemical catalytic hydrolysis of α-amino isobutyronitrile in basic solution, the following observations have been made:

(a) in a basic aqueous solution and at concentrations of reactants (α-amino isobutyronitrile acetone) of the order of 1 mole per liter, it is possible to observe NMR (nuclear magnetic resonance) at 29° C. in the normal course of the first phase of the hydrolysis reaction, the intermediate invention of the "Y" compound having 3 signals at: $\delta = 0.17$; $\delta = 0.63$ and $\delta = 0.76$, of relative strengths 2-1-1, clearly distinguished from those of the acetone ($\delta = 0.98$), of the amide ($\epsilon = 0.07$) and of the nitrile ($\epsilon = 0.25$).

(b) in a dilute alcohol solvent containing 90% of ethano and in the presence of potash, the reaction system α-amino isobutyronitrile acetone leads to α-amino isobutyramide by means of a compound characterised in ultraviolet by a wide band, the peak of which is a wavelength of less than 200 nm. This band is different from that of the amide and of the acetone.

It has also been observed that the development of this "Y" intermediary is accompanied by the formation of an equimolar quantity of α-amino isobutyramide and acetone.

(c) Finally, by repeating the above experiment from paragraph (b) but in anhydrous ethanol and in the presence of sodium ethylate it is possible not only to stabilise the product observed in ultraviolet but also to isolate it from the reaction medium in crystalline form. This compound, then placed in aqueous solution, has an NMR spectrum which is absolutely identical to the one described under (a) for the "Y" intermediary and liberates quantitatively (the reaction terminates after 5 seconds at ambient temperature) even in a neutral medium an equimolar quantity of acetone and of α-amino isobutyramide. As the pyridine flows back, or if stored for several days in the reaction medium, this compound leads on the other hand quantitatively to 2,2,4,4-tetramethyl-4-imidazolydinone, a compound which only hydrolyses very slowly when a basic solution flows back.

The three above observations demonstrate that acetone reacts on α-amino isobutyronitrile in an aqueous solution and also in an anhydrous medium to produce an identical compound which we have designated as "Y" intermediate above. Similar observations were also made when acetone was reacted with α-amino propionitrile.

Without wishing to limit the present invention by means of this interpretation, the applicant considers that the "Y" intermediary may have the following structure shown in the following reaction diagram:

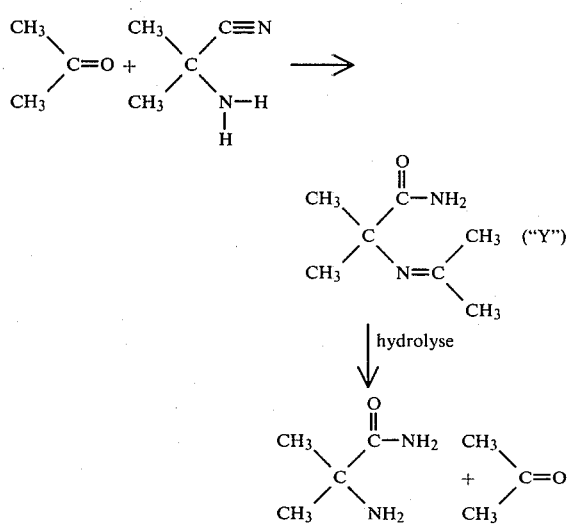

To conclude, it will be recalled simply that, on the one hand, the presence of a reaction intermediary "Y" and, on the other hand, the catalytic intervention of acetone during the hydrolysis of α-amino isobutyronitrile have been demonstrated clearly in a process which is clearly preponderating in relation to the conventional process resulting from the attack of the OH⁻ ion on the triple bond C≡N.

In this autocatalytic process, the acetone which results from the decomposition of α-amino nitrile reacts on the α-amino nitrile to finally produce by means of α-isopropylidene amino isobutyramide, the corresponding α-amino amide.

This process for chemical catalytic hydrolysis is applied particularly to the preparation of α-amino acids from the corresponding α-amino nitriles. In particular, this catalytic hydrolysis may be applied to an α-amino nitrile corresponding to the general formula (I)

in which the radical R represents a hydrogen atom or a linear or branched hydrocarbon chain containing from 1 to 12 carbon atoms and optionally 1 or more hetero atoms such as sulphur, the said radical R optionally being substituted one or more times, preferably at the end of the chain, by groups such as hydroxyl, amino, carboxyl, phenyl, hydroxyphenyl, carboxamido, indolyl, imidazolyl and guanidyl groups, or R forms with the nitrogen atom in the α-position a saturated heterocyclic group containing at least one heteroatom such as nitrogen, the said heterocyclic group itself optionally being substituted, for example by a hydroxyl group, or from any one of the salts thereof such as, for example, hydrochloride.

By introducing a sufficient quantity of hydroxide into the reaction medium in addition to the carbonyl compound and by neutralising the solution, it is possible to obtain the following α-amino acids in the form of their racemic mixtures: glycine, alanine, valine, leucine, isoleucine, phenylalanine, serine, threonine, lysine, δ-hydroxylysine, arginine, aspartic acid, asparagine, glutamic acid, glutamine, cysteine, crystine, methionine, tyrosine, thyroxine, proline, hydroxyproline, tryptophan and histidine.

The present invention will be illustrated below by means of a few embodiments of the process of the invention. These examples must of course be considered as non-limiting.

Preparation of α-amino acids from α-amino nitriles

EXAMPLE 1

Preparation of alanine from α-amino propionitrile hydroxide.

0.3 g of acetone ($5.10^{-3}$ mole) and 1 ml of soda solution 10 N are added to a solution of 0.53 g of α-amino propionitrile hydrochloride ($5.10^{-3}$ mole) in 5 ml of water. After heating the solution at 65° C. for 1 hour, the sodium salt is obtained which leads to 0.43 g of alanine after neutralisation to pH 7 with the aid of $H_2SO_4$. Yield 96.6%.

EXAMPLE 2

Preparation of methionine from α-amino methylmercaptobutyronitrile hydrochloride 0.6 g of acetone ($10^{-2}$ mole) and then 2 ml of NaOH 10 N. are added to a solution of 1.6 g of α-amino methyl mercaptobutyronitrile hydrochloride (approximately $10^{-2}$ mole) in 10 ml of water. After heating the solution at 75° C. after one hour and after subsequent neutralisation as in Example 1, the quantitative analysis of the methionine taken directly from the solution by the N.N.R. method shows a yield of 94%.

Preparation of α-amino acids from cyanohydrins

EXAMPLE 3

Preparation of alanine from lactonitrile 0.355 g of lactonitrile ($5.10^{-3}$ mole) are added to 5 ml of 0.1 molar solution of $ClNH_4$ in $NH_4OH$ 10 N. After heating at 40° for half an hour in a corked bottle, 0.3 g of acetone ($5.00^{-3}$ mole) and 0.65 ml of NaOH 10 N are added. The temperature is raised to 75° C. for one hour. The sodium salt thus obtained is then neutralised to pH 7 by means of sulphuric acid.

Quantitative analysis of the alanine by self-analysis shows a yield of 92%. The theoretical yield linked to the experimental conditions at the equilibrium is 94%.

EXAMPLE 4

Preparation of methionine from α-hydroxymethyl mercapto butyronitrile 0.65 g of α-hydroxymethyl mercapto butyronitrile ($5.10^{-3}$ mole) are added to 5 ml of a 0.2 molar solution of $ClNH_4$ and 0.1 M of KCN in $NH_4OH$ 10 N. The mixture is heated at 40° C. with magnetic agitation for an hour and a half in a closed bottle. 0.3 g of acetone ($5.10^{-3}$ mole) and 0.65 ml of NaOH 10 N are subsequently added and the temperature of the mixture is brought to 80° C. for an hour and a half still with stirring but this time the bottle is open.

After neutralisation to pH 7 by means of $H_2SO_4$, quantitative analysis of the methionine by the N.N.R. method showed a yield of 95%.

EXAMPLE 5

Preparation of phenylalanine from α-hydroxyphenyl propionitrile

Following the same mode of operation as in the above example, starting with 0.14 g (approx. $10^{-3}$ mol) of α-hydroxyphenyl propionitrile in 2 ml of 0.1 M solution in KCN and 0.2 M in $NH_4OH$ 10 N, and after adding 0.06 g of acetone and 0.11 ml of NaOH 10 N after neutralisation, quantitative analysis by an analyst of α-amino acids gave a yield of 85% of phenyl alanine.

Preparation of α-aminated acids from aldehydes or alkaline cyanide and ammonia

EXAMPLE 6

0.422 g of acetaldehyde (approx. $10^{-2}$ mole) are added to 10 ml of a 1.2 molar solution in $ClNH_4$ and 1.1 molar solution in KCN. The mixture is kept in a corked bottle at 40° C. for half an hour. 0.6 g of acetone ($10^{-2}$ mole) and 1.2 ml of NaOH 10 N are then added. The mixture is then heated to 75° C. in the open air for half an hour and the sodium salt obtained is neutralised to pH 7 by means of sulphuric acid.

Quantitative analysis of the alanine by an analyst of amino acids shows a yield of 90%.

EXAMPLE 7

0.254 (about $2.5.10^{-3}$ mole) of methyl mercapto propionaldehyde are added to 5 ml of a 0.65 molar solution in $ClNH_4$ and a 0.55 molar solution in KCN in $NH_4OH$ 10 N. The mixture is heated at 40° C. with magnetic agitation in a corked Erlenmeyer flask for an hour and a half. 0.21 g of acetone and 0.32 ml of NaOH 10 N are then added and the temperature of the mixture is brought to 80° for one hour with the bottle open.

After neutralisation, quantitative analysis of the methionine by the N.M.R. method shows a yield of 95%.

Preparation of α-amino acids from cyanohydrins in a dilute alcoholic medium

EXAMPLE 8

0.065 g ($10^{-3}$ mol) of potassium cyanide and 0.080 g ($1.5.10^{-3}$ mol) of ammonium chloride, then 1.31 g ($10^{-2}$ mol) of cyanohydrin of methyl mercapto propionaldehyde are dissolved in 5 ml of ammonia at 20% and 1 ml of ethanol. The mixture is kept in a corked ground flask at 45° C. for half an hour then for a further 20 minutes under the same conditions but after having added 0.15 ml of acetone ($2.10^{-3}$ mole) and 1.1 ml of soda 10 N. After opening the vessel, the temperature is brought to 80° C. for one hour. After neutralisation of the sodium salt obtained, quantitative analysis of the methionine in the reaction medium by the N.M.R. method shows a yield of 88% in proportion to the cyanohydrin introduced.

The above experiment produces a yield of 92% in proportion to the cyanohydrin introduced if it is repeated under the same conditions but by reducing the quantity of ethanol by half and adding 0.75 ml ($10^{-2}$ mol) of acetone instead of 0.15 ml.

The final concentration of methionine is of the order of 2 moles per liter evaporating the excess acetone and ammonia.

Preparation of an α-aminoamide from a salt of α-aminonitrile

EXAMPLE 9

Preparation of α-aminopropionamide from α-aminopropionitrile chlorohydrate

To a solution of 0.53 g of α-aminopropionitrile chlorohydrate in 5 ml of water was added 0.3 gm of acetone and 0.6 ml of 10 N soda solution. After five minutes of the reaction, determination of the RMN of the solution to show the quantitative transformation of α-aminonitrile to α-aminoamide was made. The latter compound may be recovered, by neutralisation of the solution, evaporation, and then passage of the residue on an ion-exchange column to give a yield of 95%.

Preparation of an α-aminoamides from cyanohydrins

EXAMPLE 10

Preparation of α-aminopropionamide from lactonitrile 0.355 g of lactonitrile ($5 \times 10^{-3}$ mole) are added to 5 ml of a 0.1 molar solution of ClNH$_4$ in 10 N NH$_4$OH. After heating at 40° C. for half an hour in a corked flask, 0.3 g of acetone ($5 \times 10^{-3}$ mole) and 0.1 ml of 10 N NaOH are added. The determination by RMN of the solution showed the presence of 95% of α-aminopropionamide which may be recovered by the already described method. 92% yield of recovered product.

EXAMPLE 11

Preparation of methionine amide from α-hydroxymethyl mercapto butyronitrile 0.65 g of α-hydroxymethyl mercapto butyronitrile ($5 \times 10^{-3}$ mole) was added to 5 mls of a 0.2 M solution of ClNH$_4$ and 0.1 molar KCN in 10 N NH$_4$OH. The mixture is heated to 40° C. under magnetic stirring for an hour and a half in a corked flask. Next, the flask was uncorked and 0.3 g of acetone ($5 \times 10^{-3}$ mole) and 0.1 ml of NaOH were added with magnetic stirring at ambient temperature for 10 minutes. The mixture is then neutralised and treated as previously. A yield of 95% of the α-aminoamide was obtained.

Preparation of an α-aminoamide from the alkaline cyanide of ammonia

EXAMPLE 12

0.422 g of acetaldehyde (approx $10^{-2}$ mole) were added to 10 mls of a solution of 1.2 molar ClNH$_4$ and 1.1 molar KCN in 10 N NH$_4$OH. The mixture was maintained at 40° C. for half an hour in a corked flask. After this time, 0.6 g of acetone ($10^{-2}$ mole) as well as 0.1 ml of 10 N NaOH were added. Ten minutes later the reaction mixture is neutralised and treated as previously for the recovery of the amide. Yield 91%

EXAMPLE 13

To 5 ml of a solution of 0.65 molar ClNH$_4$ and 0.55 molar KCN in 10 N NH$_4$OH was added 0.254 g (approx $2.5 \times 10^{-3}$ mole) of methylmercaptopropionaldehyde. The mixture was heated to 40° C. with magnetic stirring in an Erlenmeyer flask for 1½ hours. After this time, 0.12 g of acetone and 0.05 ml of 10 N NaOH were added.

The mixture was maintained at ambient temperature for ten minutes more, and then neutralised and treated as previously. The yield of amide recovered was 93%.

We claim:

1. In a process for the preparation of an α-amino-acid by alkaline hydrolysis of an α-amino-nitrile or one of the salts thereof, the improvement wherein said α-amino-nitrile or salt is submitted to a chemical catalytic hydrolysis by reaction in an aqueous medium of at least one ketone therewith in the presence of hydroxide ions, the ketone being introduced into said aqueous reaction medium in a proportion of from 0.1 mole to 2 moles of ketone per mole of α-amino-nitrile, and the hydroxide ions being introduced into the aqueous reaction medium so as to attain substantially the equimolarity of the hydroxide in proportion to the starting α-amino-nitrile, and wherein, after formation of the salt of α-amino-acid, the free α-amino-acid corresponding to the starting α-amino-nitrile is extracted.

2. A process according to claim 1 in which the minimum water content of the aqueous reaction medium is one mole of water per mole of α-amino-nitrile.

3. A process according to claim 1 in which said ketone is introduced into said reaction medium in a proportion of from 0.1 to 1 mole of ketone mole of per α-amino-nitrile.

4. A process according to any one of claims 1, 2 or 3 in which said chemical catalytic hydrolysis is carried out on an α-amino-nitrile corresponding to the general formula I

in which the radical R is selected from the group consisting of the hydrogen atom, linear and branched chain hydrocarbon groups containing up to 12 carbon atoms, linear and branched aliphatic chains containing up to 12 carbon atoms and at least one hetero atom of the group consisting of sulfur atoms and nitrogen atoms, linear and branched hydrocarbon chains containing up to 12 atoms and at least one substituent radical of the group consisting of hydroxyl, amino, carboxyl, phenyl, hydroxyphenyl, carboxamide, indolyl, imidazolyl and guanidyl groups, linear and branched aliphatic chains containing up to 12 carbon atoms, at least one hetero atom of the group consisting of sulfur atoms and nitrogen atoms and at least one substituent radical of the group consisting of hydroxyl, amino, carboxyl, phenyl, hydroxyphenyl, carboxamide, indolyl, imidazolyl and guanidyl groups, or in which R forms with the nitrogen atom in the α-position a pyrrolidine or hydroxypyrrolidine ring, or on a salt of said α-amino-nitrile.

5. A process according to one of claims 1, 2, 3, or 4 wherein the α-amino-nitrile reactant is the hydrochloride salt.

6. A process according to one of claims 1, 2, 3, or 4 wherein the aqueous solution also contains ethanol.

7. A process according to one of claims 1, 2, 3, or 4 wherein the ketone is selected from acetone, methyl ethyl ketone, diethyl ketone, methyl isopropyl ketone, ethyl isopropyl ketone and mixtures of these ketones.

8. A process according to one of claims 1, 2, 3, or 4 wherein the hydroxide ions are introduced into the reaction medium in the form of a hydroxide of an alkali or alkaline earth metal or ammonium hydroxide.

9. A process according to claim 1 wherein the α-amino-nitrile is prepared in situ by reacting a cyanohydrin with ammonia.

10. A process according to claim 9 wherein the equilibrium of formation of α-amino-nitrile is allowed to take place before introducing said ketone and said hydroxide ions.

11. A process according to claim 9 wherein the solution of α-amino-nitrile is stabilised by an excess of from 1 to 10% of cyanide over the amount of cyanide contained in an equimolar aldehyde-cyanide solution.

* * * * *

UNITED STATES PATENT OFFICE
CERTIFICATE OF CORRECTION

Patent No. 4,243,814  Dated January 6, 1981

Inventor(s) Robert Pascal, Monique Lasperas nee Marnier, Alain Rousset, Auguste Commeyras, Jacques Taillades and Louis Mion It is certified that error appears in the above-identified patent and that said Letters Patent are hereby corrected as shown below:

Title page, last column above [21] Appl. No. 856,320, insert --[73] Assignee: Agence Nationale De Valorisation De La Recherche (ANVAR), Neuilly S. Seine, France--

Signed and Sealed this

Fourteenth Day of June 1983

[SEAL]

Attest:

DONALD J. QUIGG

Attesting Officer

Acting Commissioner of Patents and Trademarks